(12) United States Patent
Jensdottir et al.

(10) Patent No.: US 10,660,832 B2
(45) Date of Patent: May 26, 2020

(54) ACIDIC SOLID ORAL COMPOSITIONS WITHOUT EROSIVE POTENTIAL IN SALIVA AND METHOD FOR DETERMINING EROSIVE POTENTIAL IN SALIVA

(71) Applicant: Ice Medico ehf, Reykjavik (IS)

(72) Inventors: Thorbjorg Jensdottir, Vassoy (NO); Allan Bardow Jensen, Naerum (DK); Birgitte Nauntofte, Charlottenlund (DK); Christian Buchwald, Hellerup (DK)

(73) Assignee: Ice Medico ehf, Reykjavik (IS)

( * ) Notice: Subject to any disclaimer, the term of this patent is extended or adjusted under 35 U.S.C. 154(b) by 83 days.

(21) Appl. No.: 15/485,122

(22) Filed: Apr. 11, 2017

(65) Prior Publication Data

US 2017/0216167 A1 Aug. 3, 2017

Related U.S. Application Data

(60) Division of application No. 14/062,745, filed on Oct. 24, 2013, now Pat. No. 9,651,541, which is a continuation of application No. 11/658,380, filed as application No. PCT/DK2005/000508 on Jul. 22, 2005, now abandoned.

(30) Foreign Application Priority Data

Jul. 23, 2004 (DK) .................................. 2004 01148

(51) Int. Cl.
| | | |
|---|---|---|
| *A61Q 11/00* | (2006.01) | |
| *A61K 8/18* | (2006.01) | |
| *A23G 3/00* | (2006.01) | |
| *A23G 3/36* | (2006.01) | |
| *A23G 4/00* | (2006.01) | |
| *A23G 4/06* | (2006.01) | |
| *A61K 9/00* | (2006.01) | |
| *A23G 3/34* | (2006.01) | |
| *A23G 9/32* | (2006.01) | |
| *A61K 8/02* | (2006.01) | |
| *A61K 8/19* | (2006.01) | |
| *A61K 8/365* | (2006.01) | |
| *G01N 33/50* | (2006.01) | |
| *G01N 33/84* | (2006.01) | |

(52) U.S. Cl.
CPC ................. *A61K 8/19* (2013.01); *A23G 3/34* (2013.01); *A23G 3/36* (2013.01); *A23G 3/362* (2013.01); *A23G 4/06* (2013.01); *A23G 4/064* (2013.01); *A23G 9/32* (2013.01); *A23G 9/325* (2013.01); *A61K 8/0216* (2013.01); *A61K 8/365* (2013.01); *A61K 9/0056* (2013.01); *A61Q 11/00* (2013.01); *G01N 33/50* (2013.01); *G01N 33/84* (2013.01); *A23V 2002/00* (2013.01); *A61K 2800/74* (2013.01); *A61K 2800/92* (2013.01); *G01N 2800/18* (2013.01)

(58) Field of Classification Search
CPC . A23G 3/34; A23G 3/362; A23G 4/06; A23G 4/064; A23G 9/32; A23G 9/325; A23G 3/36; A61K 8/0216; A61K 8/19; A61K 8/365; A61K 9/0056; A61K 2800/92; A61K 2800/74; A61Q 11/00; G01N 33/50; G01N 33/84; G01N 2800/18; A23V 2002/00

See application file for complete search history.

(56) References Cited

U.S. PATENT DOCUMENTS

| | | |
|---|---|---|
| 3,734,742 A | 5/1973 | Morse et al. |
| 4,080,440 A | 3/1978 | DiGiulio et al. |
| 4,820,506 A | 4/1989 | Kleinberg et al. |
| 5,028,446 A | 7/1991 | Saleeb et al. |
| 5,108,761 A | 4/1992 | Andon et al. |
| 5,468,506 A | 11/1995 | Andon |
| 6,077,557 A | 6/2000 | Gordon et al. |
| 6,120,754 A | 9/2000 | Lee et al. |
| 6,383,473 B1 | 5/2002 | Parker |
| 2003/0008054 A1 | 1/2003 | Gordon et al. |
| 2004/0091517 A1 | 5/2004 | Baker et al. |

FOREIGN PATENT DOCUMENTS

| | | |
|---|---|---|
| EP | 0 227 174 A | 7/1987 |
| EP | 0 613 684 A1 | 9/1994 |
| EP | 0 634 110 A2 | 1/1995 |
| GB | 1 516 525 | 7/1978 |
| WO | 88/03762 A1 | 6/1988 |
| WO | 97/30601 A1 | 8/1997 |
| WO | 98/13013 A1 | 4/1998 |
| WO | 99/08550 A1 | 2/1999 |

OTHER PUBLICATIONS

Bardow et al., "The bicarbonate concentration in human saliva does not exceed the plasma level under normal physiological conditions," *Clin. Oral Invest.* 4:245-253, 2000.
Jensdottir et al., "Effects of Calcium on the Erosive Potential of Acidic Candies in Saliva," *Caries Res.* 41:68-73, 2007.
Jensdottir et al., "Effects of sucking acidic candies on saliva in unilaterally irradiated pharyngeal cancer patients," *Oral Oncology* 42:317-322, 2006.
Jensdottir et al., "Effects of Sucking Acidic Candy on Whole-Mouth Saliva Composition," *Caries Res.* 39:468-474, 2005.
Tordoff, "Some Basic Psychophysics of Calcium Salt Solutions," *Chemical Senses* 21(4):417-424, Aug. 1996.

*Primary Examiner* — Lezah Roberts
(74) *Attorney, Agent, or Firm* — Seed IP Law Group LLP

(57) ABSTRACT

Acidic oral compositions having calcium contents and effective pH-values in the area indicated by grey-tone in FIG. 2 are non-erosive in saliva and capable of stimulating saliva production, even in "dry mouth" patients. A new multi-step test method for determining erosive potential in saliva has been used for identifying the compositions.

7 Claims, 2 Drawing Sheets

ACIDIC SOLID ORAL COMPOSITIONS WITHOUT EROSIVE POTENTIAL IN SALIVA AND METHOD FOR DETERMINING EROSIVE POTENTIAL IN SALIVA

BACKGROUND

Technical Field

The present invention relates in general to solid oral compositions, which provide an acidic reaction when dissolved in an aqueous liquid like saliva. More particularly, the present invention relates to acidic solid oral compositions with reduced erosive potential in saliva and to the use of a calcium component and an acid component in particular amounts for reduction of the erosive potential. The invention also relates to a method for stimulating saliva production, and to the use of a calcium component and an acid component for the manufacture of an acidic solid oral composition for alleviating the sufferings of an individual having impaired saliva production. Furthermore the invention relates to a method for determining the erosive potential of an oral composition in saliva.

Description of the Related Art

Dental erosion is the loss of dental hard tissue by a chemical process that does not involve bacteria and is therefore not associated with dental plaque. One of the most important factors with respect to dental erosion is extrinsic exposure to acid. Dental erosion has been shown to be an increasing threat to dental health, and frequent soft drink consumption as well as consumption of acid-containing foodstuffs (citrus fruits and sweets) are important factors in the development of dental erosion. The general awareness of dental erosion is increasing rapidly. It is therefore important for manufacturers to think of new ways to develop foodstuffs that satisfy consumers' need of acidic stimuli and that at the same time do not cause or reduces dental erosion.

Generally, low pH in the oral cavity and around the teeth is the major cause of dental erosion. The hard part of human teeth is composed of hydroxyapatite crystals (HAp) ($Ca_{10}(PO_4)_6(OH)_2$). In the teeth the HAp crystals are arranged in a condensed structure making up the hardest tissue in the body. However, if the teeth are exposed to fluids with a low pH (like acidic soft drinks or saliva containing dissolved acidic candy) the HAp crystals will dissolve and dental erosion will develop due to shortness of $Ca^{2+}$, $PO_4^{3-}$ and $OH^-$ ions in the fluid (components of HAp).

Beverages supplemented with significant levels of calcium for nutritional purposes have been suggested in the prior art. Dietary calcium inadequacy may be a contributing cause to osteoporosis, at least within some populations. For example, a positive correlation between calcium intake and bone mass has been found across many age groups. It has also been suggested that the level of calcium intake earlier in life directly influences the peak bone mass achieved at skeletal maturity.

U.S. Pat. No. 5,028,446 discloses a process for preparing rapidly solubilized calcium fumarate for use in the production of calcium fortified beverages. The process involves the preparation of a mixture of fumaric acid and a calcium-containing base, wherein the mole ratio of the calcium to the fumarate is ranging from 1:2 to about 1:1. The mixture of fumaric acid and calcium is indicated to possess an improved solubility characteristic usable in the production of calcium fortified beverages, such as tea.

Another calcium-fortified beverage is disclosed in EP 227 174. The beverage is substantially free of sugar alcohol and comprises a certain weight ratio of calcium to a mixture of citric, malic, and phosphoric acid of 1/4 to 1/7. The beverage is said to have a satisfactory initial taste and mouth feel, substantial freedom from objectionable aftertaste and desirable calcium absorbability/bioavailability properties. Typically, the pH of the produced beverages is around 4.3.

A dry mixture intended for reconstitution comprising citric acid and one or more calcium compounds is disclosed in WO 88/03762. The instant beverage may comprise a mole ratio of calcium/citric acid between 0.6 and about 3.0. The solubility of the mixtures having varying ratios between calcium and citric acid depended on the pH. The solubility was tested for pH values between 2.0 and 7.0, an actual drink as prepared having a pH of 4.15 and above. The composition has a utility as a liquid dietary calcium supplement.

U.S. Pat. No. 3,734,742 discloses a sealed or canned bottled aqueous beverage containing at least about 80% of water and having a pH of from 2.0 to 3.4, an ascorbic acid content of from 0.056 to 1.120 mg/ml and a ferrous ion content of from 0.008 to 0.15 mg/ml. The object of this US patent is to obtain a beverage supplemented with iron and ascorbic acid.

None of the above mentioned references relate to dental erosion.

As mentioned in the introduction, acidic compositions for consumption tend to erode tooth components, notably the content of hydroxyapatite. Several publications address this issue. EP 634 110 A2 pertains to a nutrient, vitamin and mineral fortified, fruit based liquid foodstuff having an acid content of at least 5 g/l as tartaric acid and a content of calcium phosphate of at least 2 g/l. The pH is below 4.5, with actual values between 3.9 and 4.15. The calcium phosphate is said to reduce the negative influence of the acidic liquid foodstuff on the tooth substance. Another liquid oral composition comprising a calcium compound and an acid compound is disclosed in WO 97/30601. The liquid composition contains calcium in the range of 0.3 to 0.8 moles per mole of acid and as an important feature the amount of calcium and acid in the composition is selected so that the pH of the composition is from 3.5 to 4.5. A further acidic beverage, which is said to inhibit the erosion of tooth enamel, is disclosed in U.S. Pat. No. 5,108,761. The beverage according to U.S. Pat. No. 5,108,761 includes calcium citrate malate for reduction of dental erosion.

An acidic medical preparation has been disclosed in U.S. Pat. No. 4,080,440 disclosing a process for remineralising dental enamel. The process implies applying a freshly prepared metastable aqueous solution to the tooth surface. The solution has a pH of about 2.5 to about 4.0 and comprises a soluble calcium salt and a soluble phosphate salt in such amounts that the molar ratio of calcium ions to phosphate ions is in the very broad range from 0.01 to 100. The preparation is not intended for being consumed.

Also edible or chewable solid or semi-solid compositions, which show a reduced tendency to erosion of teeth have been disclosed in the prior art. WO 98/13013 discloses e.g. a chewing gum or a candy capable of remineralising tooth lesions. The composition in question comprises a cationic component comprising at least one partially water-soluble calcium salt, an anionic component comprising at least one water-soluble phosphate salt and a separating component. The pH of the composition when dissolved in water or saliva is from greater than about 4.0 to about 10.0. Because of the partial water-solubility of the calcium salt, the calcium cations and the phosphate anions in the mixed aqueous composition remains soluble for a period of time sufficient to allow the cations and anions to diffuse through the surface of the tooth to the subsurface or dentine, where the diffused cations and anions react to form an insoluble precipitate on the lesion for remineralisation thereof.

WO 99/08550, having the same inventor as WO 97/30601, discloses an acid containing solid or semi-solid composition with reduced tooth erosion. The composition contains calcium in the range of 0.3 to 0.8 moles per mole of acid and the proportion of calcium and acid in the composition is selected so that the effective pH of the composition, when dissolved in a liquid such as water, is from 3.5 to 4.5. While a tooth protection may be obtained by using this composition, the saliva stimulating effect will be limited due to the comparatively high pH value, and the taste experience thereby impaired. This is particularly critical in relation to such products as boiled sweets, candies, lollipops, jellies, chewing gums, drops, pastilles, lozenges, tablets, ice cream and sorbets.

In U.S. Pat. No. 2004/0091517 A1 having the inventor of WO97/30601 and WO99/08550 as co-inventor, acidic oral compositions having effective pH values down to 2.2, especially acid beverages with a pH between 2.2 and 5.5, are disclosed. The invention according to said application resides in the use of a polyphosphate being a phosphate polymer wherein the number of phosphate groups (n) is at least 3, as a tooth erosion inhibitor. The polyphosphate may be used in conjunction with calcium being present in amounts up to 0.8 moles per mole of acidulant. However polyphosphates are undesirable from different points of view, particularly in the preparation of hard-boiled candy and other products, which are subjected to heating. By heating of the acidic composition there is a risk of the polyphosphate becoming converted to other phosphates, which are known to have an unpleasant taste. Furthermore, by having both calcium and phosphate in high concentrations, there is a risk of the calcium precipitating out as non-useful calcium phosphate compounds.

The present inventors suggest decreasing the pH in order to obtain a better taste experience and a pronounced saliva stimulating effect. This has been possible while maintaining a composition, which is non-erosive in saliva—without the use of a polyphosphate as disclosed in US 2004/0091517 A1.

The increased saliva production results in an increased protective effect from the constituents of the saliva itself. As a further interesting point, the non-erosive effect of the composition seems to be obtainable even in so-called "drymouth" individuals suffering from impaired saliva secretion.

This surprising finding is the result of extensive research carried out by the present inventors, which among others has resulted in a new test method for erosive potential, which in a simple and reliable manner takes into account the complex conditions in saliva in the human mouth in the presence of the acidic oral composition, such as a candy. This test method represents a particular aspect of the present invention.

When solid and semisolid compositions are sucked, saliva becomes the matrix for the compositions, and thereby saliva influences all effects that the compositions may have on teeth. The method according to the invention provides, in contrast to theoretical calculations based on physical chemistry, the unique feature of accounting for all protective factors present in human saliva, organic as well as inorganic. These factors include the salivary proteins (around 2 mg/ml), the saliva buffer capacity, the saliva calcium and phosphate, saliva fluoride, and trace amounts of other ions present in saliva. The salivary proteins have the ability to form a protective coating, also known as the acquired pellicle, on the surface of teeth. Due to this ability, the salivary proteins will protect teeth and tooth substance against acid induced erosion. However, the effect of this protein coating on tooth erosion in different individuals cannot be quantified by any known methods of calculation, it has to be subjected to testing. The saliva buffer capacity, which originates from salivary bicarbonate, phosphate, and proteins, will also protect teeth and tooth substance against acid induced erosion, and this effect also has to be accounted for by the test method. Thus, when an acidic oral composition is dissolved in saliva, the pH will drop, however, the pH drop will be counteracted by the three salivary buffer systems resulting in an increased salivary pH and thereby reduced erosive effect. Saliva also contains some calcium and phosphate, which will help to increase the degree of saturation with respect to hydroxyapatite and thereby decrease acid induced erosive effects. In this context, saliva also contains fluoride, mainly originating from foodstuffs and toothpaste, and this fluoride will increase the effective degree of saturation with respect to tooth substance, and thereby also decrease acid induced erosive effects. Finally, trace amounts of other ions originating from foodstuffs and drinking water may also have an effect on tooth substance dissolution. In concert, the three last factors may have considerable protective effects that cannot be directly predicted by calculation and therefore also needs to be tested by the method provided. The method according to the invention provides an efficient means for determining the demineralization of hydroxyapatite and thereby evaluation the erosive potential of any solid and semisolid composition dissolved in saliva.

BRIEF SUMMARY

The invention provides an acidic solid oral composition with reduced erosive potential in saliva, comprising a calcium component and an acid component, wherein the amounts of calcium component and acid component in the solid oral composition are adjusted so as to provide (i) a pH in the range of 2.2 to 3.2, when the solid oral composition is dissolved in an equal amount by weight of highly purified water, and (ii) a calcium content in the acidic solid oral composition within the following limits:

$$175-50 \cdot pH \leq \text{calcium content (mmol/kg)} \leq 660-200 \cdot pH,$$

the pH being determined as indicated above, with the proviso that the composition does not include a polyphosphate being a phosphate polymer wherein the number of phosphate groups (n) is at least 3.

It was surprisingly found that a reduced erosive potential was obtainable by a composition having a pH between 2.2 to 3.2, without the use of any polyphosphate as in US/2004/0091517 A1.

It was to be expected that the relatively long contact time between the oral solid compositions of the invention and the teeth would damage the tooth hydroxyapatite. Herein, it is reported that certain amounts of calcium component reduces the erosive potential in saliva for a composition of comparatively low pH value, even in situations where the amount of calcium results in the saliva being under-saturated with respect to calcium.

A beverage normally only has a contact time with teeth of around a few seconds before it is swallowed, whereas an oral composition intended for sucking or chewing remains in the oral cavity for several minutes. The acidic solid oral composition according to the invention allows for a substantial saliva stimulation, a better taste and at the same time, a substantively reduced erosive potential. The taste can be further improved by addition of one or more sweetening and/or flavouring agents. Such additives are also known to stimulate the saliva production.

In an aspect of the invention the saliva stimulating property of the present oral composition is used for alleviating the sufferings of individuals having impaired saliva production. Impaired saliva production can e.g. be observed in diseases such as Sjögren's syndrome, cystic fibrosis, diabetes or eating disorders, or by therapeutic treatments, such as medical treatments or radiotherapy.

Dry mouth patients commonly use acidic candies for reduction of their discomfort, but a serious drawback of the consumption of large amounts of candies is that the teeth of dry mouth patients are at a higher risk of erosion.

When healthy individuals are enjoying acidic solid oral compositions, like candies, the buffer capacity of the saliva counteracts the low pH induced by the dissolution of an oral composition. However, for patients suffering from impaired saliva production the ability to counteract the severe effect of the low pH is reduced due to low concentrations of buffers in saliva of dry mouth patients.

Therefore, there is a need for acidic oral compositions having a high ability to stimulate saliva production and being without erosive potential. The present invention suggests a solution to this need.

As used herein, the term "solid oral composition" refers to a product having a hard consistency or a gum-like consistency and which can be eaten, sucked or chewed in the oral cavity. The term solid refers to the state at the temperature of use. The present invention particularly concerns solid or semi-solid substances for oral processing such as boiled sweets, candies, tablets, lozenges, lollipops, jellies, chewing gums, drops, and the like. In an aspect of the invention, semi-solid compositions also include products such as ice cream and sorbets.

The solid oral composition according to the invention may be partially or fully soluble in water. Sweets like jellies and candies are usually fully soluble in water, whereas chewing gums usually only partially dissolves in water. When the pH of the solid oral composition is measured an amount of the composition is mixed with an equal amount by weight of highly purified water (Ph. Eur.). If necessary, the oral composition can be physically worked to obtain an aqueous phase, in which soluble components from the oral composition is dissolved. Remaining parts of the solid composition may be left in a solid phase due to saturation of the aqueous phase or insolubility of some components of the composition. A pH measured in this manner is referred to herein as "effective pH".

The actual amount of calcium component and acid component depends on the formulation of the solid oral composition of the invention. E.g. calcium lactate pentahydrate could be included in 1 kg mass for making candy, in an amount of 10 to 35 grams, corresponding to a calcium concentration of 33 to 114 mmol/kg (33 to 114 mM). The amount of acidic component is selected so as to obtain an effective pH within the range 2.2 to 3.2. The specific amount of acidic component depends on the type of acidic component, the buffer capacity of the oral composition etc. E.g., the concentration of acid component could be in the range of 33 to 132 mM (33 to 132 mmol/kg), corresponding to 5 to 20 g of tartaric acid per kg.

The calcium component is in general non-toxic and acceptable as a food supplement. Furthermore, the calcium component is in general capable of being sufficiently dissolved in the oral cavity to allow for a liberation of free calcium ions. Suitably, the calcium component is selected among calcium carbonate, calcium hydroxide, calcium citrate, calcium malate, calcium lactate, calcium chloride, calcium glycerophosphate, calcium acetate, calcium sulphate, and calcium formate, or hydrates thereof. The calcium component may also be a combination of two or more of the compounds listed above. Preferably, the calcium component is calcium lactate.

The acid component of the invention is suitably selected from the group of edible acids naturally produced in plants or animals. However, artificial acids may also be used. Preferably, the acid component is selected from the group consisting of citric acid, malic acid, ascorbic acid, tartaric acid, acetic acid, fumaric acid and lactic acid. The acid component can be added during the manufacture of the oral composition or can be present in a fruit concentrate or similar, used as base for the manufacture of the oral composition.

The amount of acid used in the manufacture of the solid oral composition of the invention, is suitably selected so as to provide a certain predetermined pH, when the oral composition is dissolved in an equal amount by weight of highly purified water, e.g. Millipore® water. Millipore® water is demineralised, distilled, filtrated and ion-exchanged water, which has furthermore been subjected to reverse osmosis. For the purpose of this pH measurement it is of importance that the water does not contain buffer salts. According to the invention the acid is adjusted in the oral composition in such manner that the effective pH is between 2.2 and 3.2. In a preferred aspect, the effective pH is between 2.5 and 3.2, particularly between 2.6 and 3.1.

Acidic solid oral compositions according to the invention have mole ratios of calcium component to acid component within the range from 0.1 to 1.40 and preferably between 0.3 and 0.8. More preferred the mole ratio of calcium component to acid component is between 0.4 and 0.7.

The composition of the invention may be composed of just the calcium and the acid component. Suitably, however, the calcium and the acid component are comprised in a carrier. The carrier may e.g. form a vitreous, crystalline, or gum-like basic structure. The choice of carrier depends on the product intended. F. inst. a carrier forming a vitreous or crystalline structure may be selected, when a candy is produced and a carrier forming a gum-like structure may be selected, when the product is a chewing gum or a jelly.

Typically, a sugar and/or a sugar substitute is selected as the carrier when a candy is produced. Suitable sugars include sucrose, isomalt, maltose, glucose, fructose, invert sugar, syrup, etc. The sugar substitute, or sweetener, may e.g. be selected among saccharin, dextrose, levulose, sodium cyclamate, Acesulfame-K and aspartame. The sugar component may be a mixture of a sugar and a sweetener. The sugar component may also be a combination of different sugars. In accordance with one aspect of the invention a candy is produced by dissolution of a sugar component in water followed by cooking of the solution until so much water has evaporated that a temperature of 105 to 160° C. is obtained. The mixture is now viscous and referred to as a dough. The acid component and the calcium component are added to the dough followed by mixing. Usually, the dough is also mixed with a flavouring agent and a colour. The dough is then cut into appropriate pieces and allowed to cool.

A jelly is usually based on gelatine. However, other polymers having a natural origin or synthetic polymers may also be used. Initially, the gelatine is dissolved in water followed by addition of sugar components, e.g. sucrose or glucose syrup or any of the other sugar components mentioned above. The homogenous mixture is then boiled until a certain dry matter content is obtained, due to evaporation of water. Then the remaining components are added to the mixture, including the calcium and the acid component. Flavour and colour is normally added at this stage. After thorough mixing the blend is cast or extruded to suitable forms.

As mentioned above, the erosive potential of a composition in a complex fluid like saliva cannot be theoretically calculated, but will have to be tested.

For testing of the erosive potential a new test method has been developed, which in a simple and reliable manner takes into account the effect of the oral composition on the production and composition of the saliva under in vivo conditions. This new test method represents a particular aspect of the present invention.

Accordingly the present invention provides a method for determining the erosive potential in saliva of an oral composition, comprising the steps of:
a) bringing the oral composition to be tested into contact with saliva in the mouth,
b) collecting a sample of the saliva under conditions so as to prevent $CO_2$ from escaping from the sample,
c) measuring the pH of the sample collected under b),
d) removing $CO_2$ from the sample, optionally assisted by vacuum and/or addition of a non-volatile acid,
e) adjusting the pH of the sample to the value measured under c) using a non-volatile acid or, if necessary, a non-volatile base,
f) adding tooth substance to the sample obtained from step e), and observing any rise in the pH,
g) if a rise in pH is observed in step f), titrating the sample to the pH value measured in c) using an acid, and
h) calculating the amount of tooth substance eroded based on the amount of acid consumed in step g).

The initial measurement of the pH in step c) may be performed in any suitable way. As an example, a pH electrode may be present in the mouth cavity to record the pH at the time the sample is taken. However, to increase the user convenience the saliva sample is typically collected in a closed system preventing $CO_2$ from escaping from the sample. A suitable way of collecting the sample is to use a syringe for withdrawal from the mouth cavity of a suitable amount of saliva. A sample of saliva from the mouth cavity of the test person is usually taken prior to administering the oral composition. Then the oral composition to be tested is brought into contact with saliva in the mouth for an adequate period. In case of a solid oral composition, the oral composition is sucked or chewed habitually for an adequate period of time before a saliva sample is withdrawn. A single or multiple samples may be collected. Multiple samples could e.g. be collected by collecting a sample every 30 seconds or every minute for a total of five minutes. In the event only a single sample is collected it may suitably be withdrawn after it has been secured that sufficient oral composition has dissolved in the saliva of the mouth, e.g. after 3 minutes. During the entire test period the test person is requested not to swallow the oral composition or any saliva.

After measuring the pH, the $CO_2$ is removed from the sample. Various methods for removing $CO_2$ are available for the skilled person, including sonification, vacuum treatment, and stripping. Generally, vacuum is used together with stirring. The $CO_2$ removal may be assisted by addition of a non-volatile acid. The non-volatile acid is usually a strong acid. The strong acid can be selected from the group consisting of aqueous solutions of HCl or $HNO_3$. When the $CO_2$ has been removed, the pH of the sample is adjusted to the pH originally measured using a non-volatile acid or, if necessary, a non-volatile base. The latter may e.g. be relevant, if the amount of non-volatile acid added for assisting the removal of $CO_2$ has brought the pH of the sample below the pH value measured under c).

The saliva sample has now been depleted of its content of $CO_2$ but retained its original acidity. Next, a tooth substance is added to test whether any erosion occurs. The tooth substance can originate from humans or animals or can be artificial. If the tooth material originates from humans or animals, it is usually ground to obtain a high surface area. It is, however, preferred to use artificial tooth substances, i.e. substances of non-dental origin, in order to avoid the variation appearing between individuals. The primary component of enamel and dentin in teeth is hydroxyapatite. Thus, in a preferred embodiment, hydroxyapatite is selected as the tooth substance, particularly hydroxyapatite $(Ca_{10}(PO_4)_6(OH)_2)$ with a solubility product of approximately 117.3 (pK) at SATP (Standard Ambient Temperature and Pressure).

The tooth substance can be left in the saliva for a certain period of time before the titration is performed. Due to the thermodynamic nature of the solubility product of hydroxyapatite, the sample should be kept at a temperature, not higher than body temperature and not lower than 20° C., until the titration is performed.

The amount of acid used for the titration is equivalent to the amount of dissolved tooth substance. Thus, 1 mM hydroxyapatite ($M_W$ 1005) requires 14 mM $H^+$ ($M_W$ 1) due to the reaction: $Ca_{10}(PO_4)_6(OH)_2 \rightarrow 10Ca^{2+}+6PO_4^{3-}+2OH^- \rightarrow 10Ca^{2+}+6H_2PO_4^-+2H_2O$, provided that the pH in the saliva is in the range from 3 to 5. Therefore the use of 14 μl 1N acid, such as 1M HCl (i.e. 14 μg $H^+$) for back titration reflects the dissolution of 1005 μg hydroxyapatite, and the use of 1 μl 1M HCl reflects the dissolution of 72 μg HAp (i.e. 1005/14).

Accordingly, the amount of hydroxyapatite crystals lost per minute in the candy containing saliva could be back calculated from the number of μl 1M HCl needed to reach the pH obtained in step c) by the following equation:

$$\mu g\ HAp\ lost = (\mu l\ acid\ used \times 72)/minutes\ of\ dissolution$$

In the event the solid oral composition does not provoke any rise in the pH in step f) the method is not continued to steps g) and h) and it is concluded that the tested oral composition is non-erosive. If however, a pH rise in step f) is observed, steps g) and h) provide a quantification of the amount of lost (or eroded) hydroxyapatite.

The method provides the unique feature of accounting for the influence of the complex conditions in saliva in the human mouth on dental erosion. Furthermore, the variable contribution of $CO_2$ in the samples to the pH over time is avoided. As the pH is the most important single factor in relation to erosion of teeth, the present method provides an efficient means for predicting the demineralisation of hydroxyapatite and thereby evaluating the erosive potential in saliva.

Acidic solid oral compositions according to the invention, which, when tested by the method according to the invention in randomly selected healthy test persons, do not result in any rise in pH in step f) within a period of 5 minutes for at least 90% of the test persons, represent a preferred aspect.

As will appear from the explanations given above, the erosive potential of a composition in saliva cannot be theoretically calculated, but will have to be tested. However based on experiments with compositions, which have been shown to be non-erosive, the following correlation between the amount of calcium component and the effective pH was initially found:

calcium content (mM)=650±10−200·pH

The actual pH-ranges, within which the correlation applied were not established initially, but at least the correlation was expected to exist within the pH-range from 2.6 to 3.1.

Later experiments have confirmed this pH range and even broadened it to pH 2.2 to 3.2. Likewise the range of calcium content in mM or mmol/kg has been broadened to:

175−50·pH≤calcium content (mmol/kg)≤660−200·pH.

The pH value is the pH obtained when the solid oral composition is dissolved in an equal amount by weight of highly purified water, i.e. the "effective pH".

Figure 2:
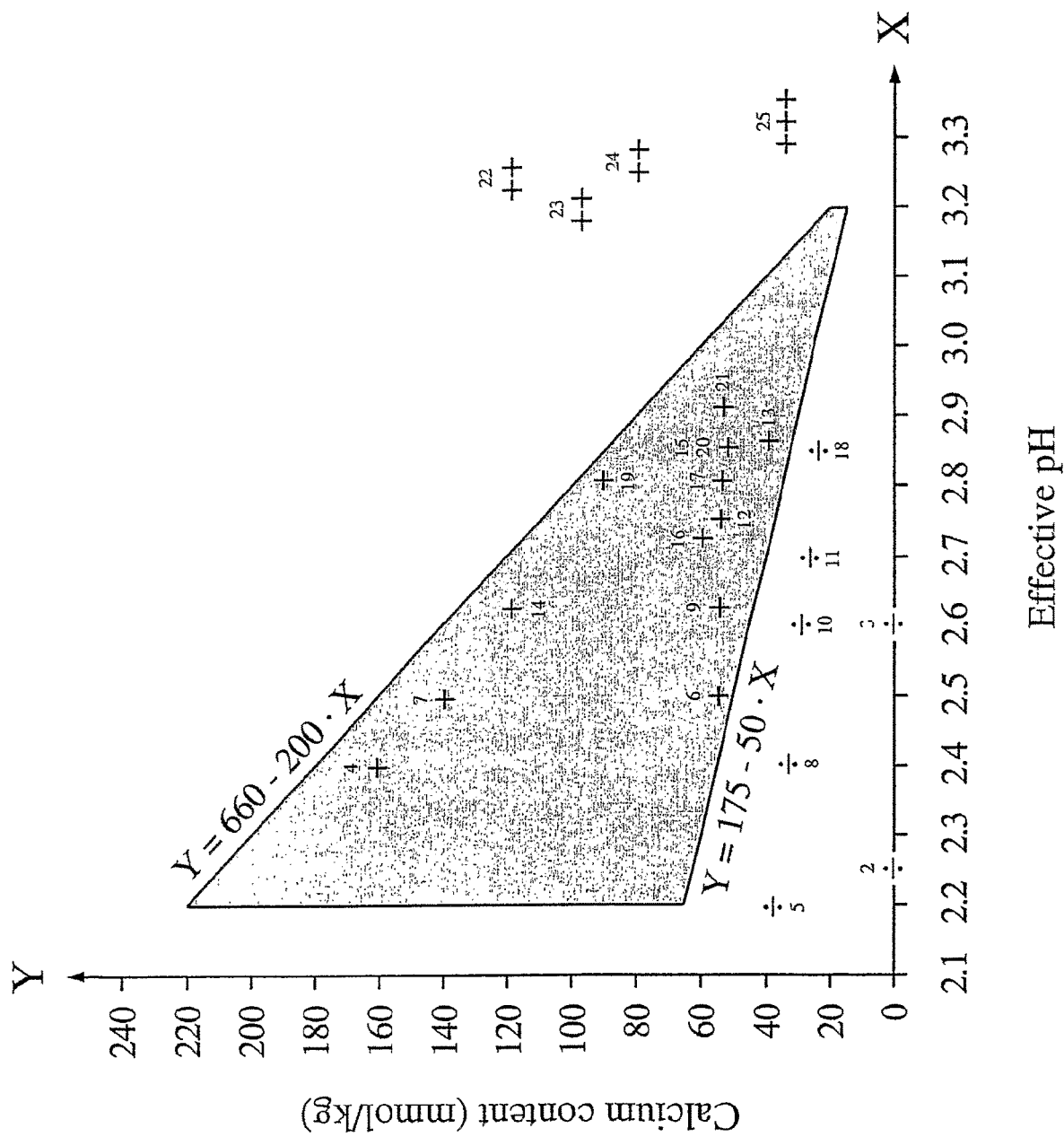
FIG. 2 is a graphic representation illustrating calcium content in mmol/kg versus effective pH for compositions according to the invention as well as some compositions, which are not according to the invention.

The correlation between effective pH and calcium content in mmol/kg has been illustrated graphically in FIG. 2.

In the following the invention will be further described by examples, which shall not be regarded as limiting for the scope of the invention.

EXAMPLES

Example 1

Preparation of Solid Candy

In a mini cooker 800 ml water is added 3 kg isomalt and 0.3 mg sweetener (Acesulfame-K) during stirring. The stirring is continued until a homogenous solution is obtained. Subsequently the temperature is raised to about 162° C. and the mixture is boiled. When the temperature has decreased to 110° C. the stirring is discontinued and the dough is withdrawn from the mini cooker and applied on a heated table.

The dough is added 4.5 ml red colour (camine E120) and kneaded so as to obtain a uniform distribution of the colour. Then, 6 ml aroma (strawberry and rhubarb in 2:1 ratio) is added and kneaded into the dough. Subsequently, 30 g tartaric acid (mol weight: 151 g/mol) and 49.5 g calcium lactate penta hydrate (mol weight: 308 g/mol) are added and mixed thoroughly with the dough. Long strings of dough are prepared and cut into appropriate pieces of candy. The candy is allowed to cool to room temperature.

A candy was added an equal amount by weight of water (Millipore®), i.e a 1:1 ratio of candy and water was formed, and allowed to stand for 1 hour. After an hour the candy was completely dissolved. In the resulting solution the pH was measured with a calibrated electrode to 2.95.

The mole ratio of calcium component to acid component can then be calculated as $$\frac{49.5 \text{ g calcium lactate penta hydrate}/308 \text{ g/mole}}{30 \text{ g tartaric acid}/151 \text{ g/mole}} = 0.82$$

Example 2

Preparation of Jellies 8 g gelatine (250 Bloom) is dissolved completely in 17 g 80° C. water under constant stirring. 4 g dextrose is added to the gelatine solution under constant stirring until the mixture is homogenous. Then, 20 g sucrose and 49 g glucose syrup (48 DE) are added and the stirring is continued until the mixture is homogeneous. This mixture is then boiled until brix 75, which happened at 108° C. (vacuum at 0.6 atm). After the boiling step the mixture is added 10 g tartaric acid (mol weight: 151 g/mol), 16.5 g calcium lactate penta hydrate (mol weight: 308 g/mol), 0.15 ml red colour (camine E120) and 0.6 ml aroma (strawberry and rhubarb in 2:1 ratio) and mixed to obtain a homogenous solution. The pH in the liquid mixture is adjusted with tartaric acid to a pH of 3.2 as measured with a standard pH electrode. A sample was withdrawn and mixed with an equal amount by weight of water. The pH of this diluted sample was measured as pH 3.2. The mole ratio of calcium component to acid component is $$\frac{16.5 \text{ g calcium lactate penta hydrate}/308 \text{ g/mole}}{10 \text{ g tartaric acid}/151 \text{ g/mole}} = 0.82$$

The solution is cast in an adequate shape and allowed to cool to room temperature.

Example 3

Test for Erosive Potential of Oral Composition

Candies as produced in example 1 were used in this example to illustrate the erosive potential. A control candy comprising the same components as the example 1 candy except for calcium lactate was also produced.

Ten randomly selected healthy test persons (5 males and 5 females) sucked 5 grams of the candy habitually for 5 minutes while his/her stimulated whole mouth saliva was collected every 30 seconds for 5 minutes. A closed saliva collection system was used to avoid saliva $CO_2$ evaporation and thus pH changes during collection.

Immediately after collection, the pH of the saliva was determined in a closed system, and the pH was recorded for each of the collections (i.e. first min, second min, etc.). The saliva was then poured into an open glass and salivary $CO_2$ was removed by vacuum during constant stirring and the sample was acidified (1M HCl) until the pH obtained immediately after collection was reached.

Pure hydroxyapatite crystals (HAp) equal to 2 mg per ml saliva (i.e. 2 mM HAp) were added to each of the saliva samples. The grain size of the HAP crystals was 1 μm and they were supplied by Merck Crystals. The pH rise, if any, was recorded continuously at 15-second interval for 5 minutes at room temperature. The test procedures mimic an in vivo condition, which is comparable to sucking on 5 gram of the candy for 5 minutes in vivo.

In case there was no pH rise, the hard-boiled candy was assessed as non-erosive.

A pH rise indicated that dissolution of HAp crystals had taken place and that the candy was erosive. To quantify the amount of dissolved HAp a back titration with acid (1M HCl) was performed 5 minutes after the HAP addition. The amount of HAp crystals lost per minute in the candy containing saliva could then be calculated from the amount of μl 1M HCl needed to reach the pH obtained immediately after collection of saliva using the equation stated in example 2.

Figure 1:
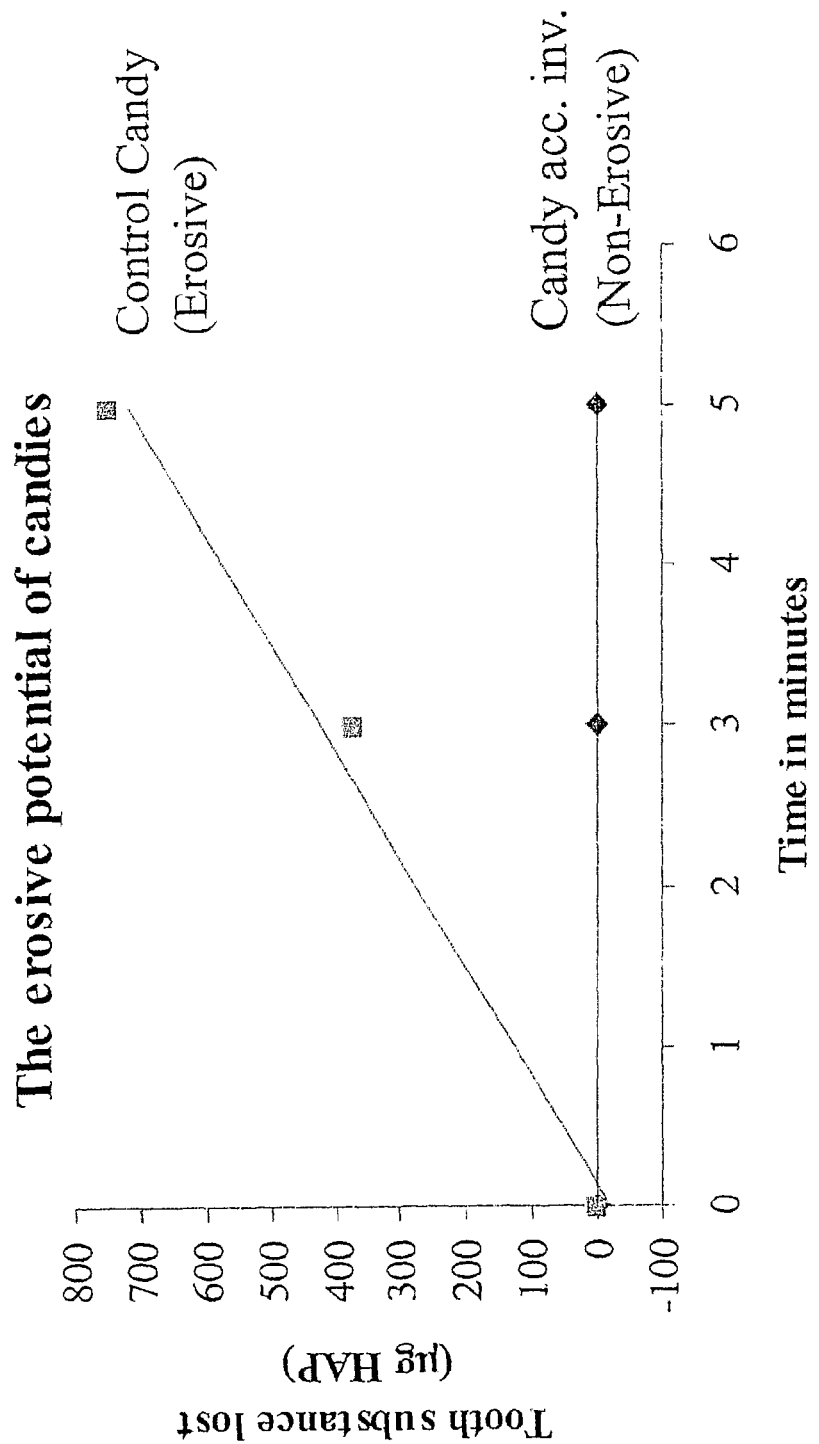
FIG. 1 illustrates the amount of tooth substance lost by dental erosion versus time by testing of a candy according to the invention and a control candy, respectively.

From the data obtained the erosive potential can be computed as the slope of curve (μg HAp lost per minute of exposure for candy containing saliva) by linear regression. The result of the experiment is shown on FIG. 1, in which the candy acc. inv. is the candy according to example 1 and the control candy is the candy lacking calcium lactate. The results show that the calcium-modified candy according to the invention was acidic as well as non-erosive due to the interplay between calcium component, saliva buffer capacity, and salivary protein protection.

Example 4

Candies of the compositions indicated in Table 1 were prepared in a similar manner to Example 1 and tested for erosive potential using the test method described in example 3 with the results likewise indicated in the table.

and $Y=175-50 \cdot X$ in the range from $X=2.2$ to $3.2$ (marked in grey tone) illustrates compositions according to the invention (marked with +), i.e. compositions, which have qualified as non-erosive in human saliva by the above test, have an adequate acidity to provide the desired saliva secretion stimulation, and a calcium content, which is sufficiently low to provide an agreeable taste. Compositions marked by ÷ have been found erosive, whereas compositions marked by ++ have been found non-erosive, but with an unacceptable taste because of an excessive amount of calcium, and the composition marked by +++ non-erosive, but with too low acidity to provide the desired saliva secretion stimulation.

Example 5

Test for Saliva Stimulating Effect

A group of 20 healthy individuals was given a candy of the composition according to test 21, and the amount of saliva produced by sucking the candy was recorded. The amount of saliva produced by sucking the candy was compared with the amount of saliva produced by the same individuals within the same period of time without any stimulation of the saliva production. The test showed a more than tenfold increase in saliva production by sucking the candy.

A corresponding test carried out on a group of 10 dry mouth patients showed a fold increase in saliva production by sucking a candy of the composition according to test 21.

TABLE 1

| Test | Ca comp. (g) | Ca (mmol/kg) | Acid comp. (g) | Acid (mmol/kg) | Ca/acid mole ratio | Effective pH | Erosive |
|---|---|---|---|---|---|---|---|
| 1 | 0.0 | 0 | 7.0 | 47 | 0.00 | 2.00 | YES |
| 2 | 0.0 | 0 | 5.0 | 33 | 0.00 | 2.25 | YES |
| 3 | 0.0 | 0 | 3.0 | 20 | 0.00 | 2.60 | YES |
| 4 | 49.1 | 160 | 60.2 | 400 | 0.40 | 2.40 | NO |
| 5 | 11.0 | 36 | 13.0 | 87 | 0.41 | 2.20 | YES |
| 6 | 16.5 | 54 | 18.0 | 120 | 0.45 | 2.50 | NO |
| 7 | 43.0 | 140 | 46.8 | 311 | 0.45 | 2.50 | NO |
| 8 | 10.0 | 33 | 10.0 | 67 | 0.49 | 2.40 | YES |
| 9 | 16.5 | 54 | 16.0 | 107 | 0.50 | 2.64 | NO |
| 10 | 9.0 | 29 | 8.0 | 53 | 0.55 | 2.60 | YES |
| 11 | 8.1 | 26 | 7.0 | 47 | 0.56 | 2.70 | YES |
| 12 | 16.5 | 54 | 14.0 | 93 | 0.57 | 2.76 | NO |
| 13 | 12.3 | 40 | 10.0 | 67 | 0.60 | 2.87 | NO |
| 14 | 36.8 | 120 | 30.1 | 200 | 0.60 | 2.64 | NO |
| 15 | 15.4 | 50 | 12.5 | 83 | 0.60 | 2.84 | NO |
| 16 | 18.5 | 60 | 15.0 | 100 | 0.60 | 2.73 | NO |
| 17 | 16.5 | 54 | 12.0 | 80 | 0.67 | 2.81 | NO |
| 18 | 7.0 | 23 | 5.0 | 33 | 0.68 | 2.85 | YES |
| 19 | 27.6 | 90 | 22.1 | 147 | 0.70 | 2.81 | NO |
| 20 | 15.0 | 49 | 10.0 | 67 | 0.73 | 2.87 | NO |
| 21 | 16.5 | 54 | 10.0 | 67 | 0.80 | 2.91 | NO |
| 22 | 37.0 | 120 | 15.0 | 100 | 1.20 | 3.24 | NO |
| 23 | 31.0 | 101 | 12.5 | 83 | 1.21 | 3.20 | NO |
| 24 | 25.0 | 81 | 10.0 | 67 | 1.22 | 3.27 | NO |
| 25 | 10.7 | 35 | 7.3 | 48 | 1.25 | 3.32 | NO |

Some of the compositions, which were found non-erosive by the test, were found unsatisfactory from other points of view, either because of the effective pH being too high to give an adequate saliva stimulating effect or because of the calcium content being to high to give an acceptable taste.

The correlation between effective pH and calcium content in mmol/kg for tests 1-25 has been illustrated graphically in FIG. 2, wherein the area between the lines $Y=660-200 \cdot X$

The invention claimed is:

1. A method for determining dental erosive potential in saliva of an oral composition in a human mouth, comprising the steps of:
   (a) bringing the oral composition to be tested into contact with saliva in the mouth,
   (b) collecting a sample of the saliva under conditions so as to prevent $CO_2$ from escaping from the sample, (c) measuring pH of the sample collected in step (b) to obtain a pH value,
(d) removing $CO_2$ from the sample collected in step (b),
(e) adjusting pH of the sample from which $CO_2$ has been removed in step (d) to the pH value measured in step (c), by adding a non-volatile acid or a non-volatile base, to obtain a pH-adjusted sample,
(f) adding tooth substance to the pH-adjusted sample obtained from step (e), and observing any rise in pH of the pH-adjusted sample,
(g) if a rise in pH is observed in the sample of step (f), titrating the sample to the pH value measured in (c) using an acid to determine an amount of the acid that is consumed, and
(h) calculating an amount of tooth substance eroded based on the amount of acid consumed in step (g).

2. The method according to claim 1, wherein the tooth substance is hydroxyapatite.

3. The method according to claim 2, wherein the hydroxyapatite is of non-dental origin.

4. The method according to claim 1, wherein the acid used for titrating in step (g) is HCl.

5. The method of claim 1 wherein step (d) of removing is assisted by at least one of: (i) vacuum treatment, and (ii) addition of a non-volatile acid.

6. The method of claim 5, wherein the non-volatile acid is a strong acid.

7. The method of claim 5, wherein the non-volatile acid is HCl or $HNO_3$.

\* \* \* \* \*